United States Patent
Xu et al.

(10) Patent No.: US 6,339,161 B1
(45) Date of Patent: Jan. 15, 2002

(54) GROUP 8, 9 OR 10 TRANSITION METAL CATALYST FOR OLEFIN POLYMERIZATION

(75) Inventors: Wei Xu; Qinyan Wang; Ryan Paul Wurz, all of Calgary (CA)

(73) Assignee: Nova Chemicals (International) S.A. (CH)

(*) Notice: Subject to any disclaimer, the term of this patent is extended or adjusted under 35 U.S.C. 154(b) by 0 days.

(21) Appl. No.: 09/788,961

(22) Filed: Feb. 19, 2001

Related U.S. Application Data

(62) Division of application No. 09/296,890, filed on Apr. 22, 1999, now Pat. No. 6,239,237.

(51) Int. Cl.$^7$ .................. C07D 327/00; C07D 333/00; C07D 305/00; C07D 307/02; C07F 9/02

(52) U.S. Cl. .................. 549/3; 549/6; 549/61; 549/74; 549/214; 549/216; 549/474; 549/476; 549/491; 558/73; 502/155

(58) Field of Search ................ 549/3, 6, 61, 74, 549/214, 216, 474, 476, 491; 558/73

(56) References Cited

U.S. PATENT DOCUMENTS

| | | | |
|---|---|---|---|
| 5,557,023 A | | 9/1996 | Somogyvari et al. |
| 5,589,555 A | | 12/1996 | Zboril et al. |
| 6,136,743 A | * | 10/2000 | Sugimura et al. ........... 502/113 |
| 6,153,758 A | * | 11/2000 | Sannicolo et al. .......... 548/111 |
| 6,187,910 B1 | * | 2/2001 | Kasina ........................ 534/10 |
| 6,218,558 B1 | * | 4/2001 | Kato et al. .................... 556/12 |
| 6,225,487 B1 | * | 5/2001 | Guram ........................ 556/18 |
| 6,245,871 B1 | * | 6/2001 | Mackenzie et al. ......... 526/141 |
| 6,288,253 B1 | * | 9/2001 | Manzer et al. ................ 556/9 |

FOREIGN PATENT DOCUMENTS

| | | |
|---|---|---|
| EP | 1 004 600 A | 5/2000 |
| WO | WO 98/27124 | 6/1998 |
| WO | WO 98/30609 | 7/1998 |
| WO | WO 98/47933 | 10/1998 |
| WO | WO 98/49208 | 11/1998 |

OTHER PUBLICATIONS

M.W. Avis, K. Vrieze, H. Kooijman, N. Veldman, A.L. Spek, And C.J. Elsevier, Selective Formation of Four–Membered Metallacyclic Pt–N–P–C Compounds from Reactions of Bis (N–arylimino) phosphor–anyl) methanes with Halide–Bridged Platinum (II) Phosphine Dimers. Inorg. Chem. 1995,34, 4092–4105.

M.W. Avis, C.J. Elsevier, N. Veldman, H. Kooijman, and A.L. Spek Monodentate o–N and Bidentate o–N,o–N Coordination of 1,1–Bis (N–p–tolylimino) diphenylphosphoranyl)ethane, $CHCH_3(PPh_2=NC_6H_4-4-CH_3)_2$, to Platinum(II), Inorg. Che. 1996, 35, 1518–1528.

M.W.Avis, M.E. Van Der Boom, C.J. Elsevier, W.J.J. Smeets and A.L. Spek, Reactions of bis(iminophosphoranes) with palladium (II) dichloride; metal–induced tautomerization orthopalladation and unexpected platinum–assisted [2+2] cycloaddition of an aryl–nitrile with a phosphinimine moiety, Journal of Organmetallic Chemistry 527 (1997) 263–276.

B.L. Small, J. Brookhart and A.M.A. Bennett, Highly Active Iron and Cobalt Catalysts for the Polymerization of Ethylene, J. Am. Chem. Soc. 1998, 120, 4049–4050.

G.J.P. Britovsek, V.C. Gibson, B.S. Kimberley, P.J.Maddox, S.J. McTavish, G.A. Solan, A.J.P. White and D.J. Williams, Novel olefin polymerization catalysts based on iron and cobalt, Chem. Commun., 1998, 849.

P.Imhoff, S.G.A. Nefkens, and C.J. Elsevier, Stabilization of Rhodium(I)—and Iridium(I)–Alkyl Bonds by Intramolecular Coordination of an Iminophosphorance. Organmetallics 1991, 10, 1421–1431.

* cited by examiner

*Primary Examiner*—Deborah C. Lambkin
(74) *Attorney, Agent, or Firm*—Kenneth H. Johnson

(57) ABSTRACT

Olefin co- or homopolymers having a good molecular weight and short chain branching may be prepared in the presence of a tridentate complex of a Group 8, 9 or 10 metal.

6 Claims, No Drawings

GROUP 8, 9 OR 10 TRANSITION METAL CATALYST FOR OLEFIN POLYMERIZATION

This application is a division of 09/296,890 Apr. 22, 1999 U.S. Pat. No. 6,239,237.

FIELD OF THE INVENTION

The present invention relates to late transition metal complexes; a process for their preparation and their use in the polymerization of olefins.

BACKGROUND OF THE INVENTION

The papers Organometallics, 10, 1421–1431, 1991; Inorg. Chem., 34, 4092–4105, 1995; J. Organomet. Chem., 527 (1–2), 263–276, 1997; and Inorg. Chem., 35(6), 1518–28, 1996, report the reaction of bis (iminophosphoranyl) methane (BIPM) which are typically aryl substituted on the phosphorus atom and the nitrogen with group VIII metal halides (chlorides) further comprising at two weakly coordinating ligands (L) such as nitriles or cyclooctadiene, afforded several products depending on the reaction time, type of ligand or nature of the metal. The product could be a N—C chelating type product or a N—N chelating product (similar to those of the present invention).

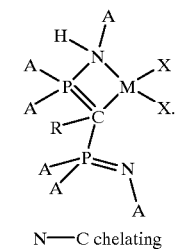

N—C chelating

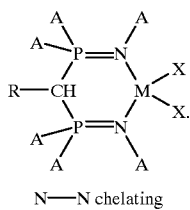

N—N chelating

The products contain alkyl bridge between the phosphinimine groups and the references do not disclose the tridentate transition metal complexes of the present invention. Further, none of the references teach or suggest the use of such compounds for the polymerization of alpha olefins.

U.S. Pat. No. 5,557,023 issued Sep., 1996 teaches the use of some phosphinimines complexes to oligomerize alpha olefins. However, the complexes disclosed are not bis-imine complexes. Rather, the complexes are of the structure indicated below.

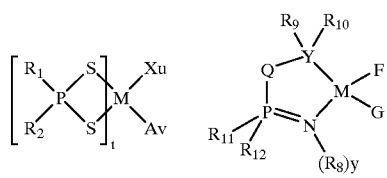

-continued

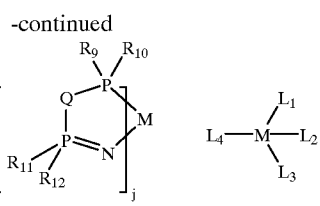

wherein R, Q, etc. are as defined in the patent. The structures disclosed in the patent are not the bis-imines of the present invention. While the reference does teach oligomerization, it does not suggest polymerization.

WO 98/30609 patent application published Jul. 16, 1998 assigned to E. I. Du Pont de Nemours teaches the use of various complexes of nickel to polymerize alpha olefins. A close complex in the disclosure is compound XXXXI at the middle of page 9 and the associated description of the various substituents. While, the compound contains a cyclic bridge, a nickel heteroatom completes the cyclic bridge in the middle of the compound. The reference does not contemplate or disclose compounds of the present invention which have a tridentate functionality. The reference fails to disclose the subject matter of the present invention.

There are a number of patents and papers by Brookhart and/or Gibson disclosing the use of pyridine bridged bis-amine Group 8, 9 or 10 metals to polymerize olefins. However, such papers teach that copolymers are not produced (e.g. WO 98/27124). The present invention proved copolymers of olefins made using an iron (or cobalt) based catalyst.

WO 98/47933 published Oct. 29, 1998 to MacKenzie et al, assigned to Eastman Chemical Company teaches bidentate amino-imine complexes of iron, cobalt, nickel and palladium for the polymerization of olefins. The complexes do not contemplate the presence of a sulfur, oxygen or phosphorus atom in the ligand bound to the iron, cobalt, nickel or palladium metal atom. As such the reference teaches away from the subject matter of the present invention.

WO 98/49208 published Nov. 5, 1998 in the name of Bres et al, assigned to BP Chemicals Limited also discloses an amino-imine complex of nickel or palladium for the polymerization of alpha olefins. Again the reference teaches away from the subject matter of the present invention in that it does not teach nor suggest the presence of a sulfur, oxygen or phosphorus atom bound to the metal atom in the complex.

SUMMARY OF THE INVENTION

The present invention provides a ligand of formula I:

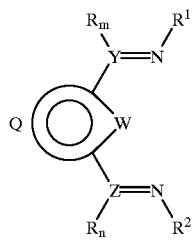

wherein W is selected from the group consisting of a sulfur atom, an oxygen atom and a phosphorus atom; Y and Z are independently selected from the group consisting of a carbon atom, a phosphorus atom and a sulfur atom; when Y is phosphorus m is 2, when Y is carbon or sulfur m is 1; when Z is phosphorus n is 2, when Z is carbon or sulfur n is 1; each R is independently selected from the group consisting of a hydrogen atom, and a hydrocarbyl radical or R taken together with Q may form a cyclic hydrocarbyl; $R^1$ and $R^2$ are independently selected from the group consisting of a hydrogen atom, a substituted or unsubstituted hydrocarbyl radical which may contain one or more heteroatoms, preferably consisting of the group selected from silicon, boron, phosphorus, nitrogen and oxygen which may be bound directly or indirectly to the nitrogen atoms and a tri-$C_{1-4}$ alkyl silyl radical; Q is a divalent unsaturated hydrocarbyl radical or a divalent radical comprising hydrogen, carbon and one or more heteroatoms selected from the group consisting of an oxygen atom, a nitrogen atom, a sulfur atom and a boron atom, and Q when taken together with W forms one or more unsaturated rings, which unsaturated cyclic rings may be unsubstituted or may be fully substituted by one or more substituents independently selected from the group consisting of a halogen atom and an alkyl radical.

The present invention further provides a process for the polymerization of one or more $C_{2-12}$ alpha olefins in the presence of an activated complex of formula II:

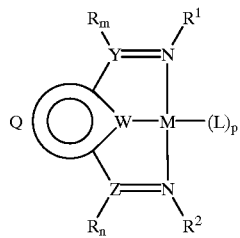

wherein M is a Group 8, 9 or 10 metal; W is selected from the group consisting of a sulfur atom, an oxygen atom and a phosphorus atom; Y and Z are independently selected from the group consisting of a carbon atom, a phosphorus atom and a sulfur atom; when Y is phosphorus m is 2, when Y is carbon or sulfur m is 1; when Z is phosphorus n is 2, when Z is carbon or sulfur n is 1; each R is independently selected from the group consisting of a hydrogen atom, and a hydrocarbyl radical or R taken together with Q may form a cyclic hydrocarbyl; $R^1$ and $R^2$ are independently selected from the group consisting of a hydrogen atom, a substituted or unsubstituted hydrocarbyl radical which may contain one or more heteroatoms, preferably consisting of the group selected from silicon, boron, phosphorus, nitrogen and oxygen which may be bound directly or indirectly to the nitrogen atoms and a tri-$C_{1-4}$ alkyl silyl radical; Q is a divalent unsaturated hydrocarbyl radical or a divalent radical comprising hydrogen, carbon and one or more heteroatoms selected from the group consisting of an oxygen atom, a nitrogen atom, a sulfur atom and a boron atom, and Q when taken together with W one or more unsaturated rings, which unsaturated cyclic rings may be unsubstituted or may be fully substituted by one or more substituents independently selected from the group consisting of a halogen atom and an alkyl radical, L is an activatable ligand and p is an integer from 1 to 3.

In a further aspect, the present invention provides a process for reacting one or more $C_{2-12}$ alpha olefins in a nonpolar solvent in the presence of the above catalyst with an activator at a temperature from 20° C. to 250° C.; and at a pressure from 15 to 15000 psi.

DETAILED DESCRIPTION

The term "scavenger" as used in this specification is meant to include those compounds effective for removing polar impurities from the reaction solvent. Such impurities can be inadvertently introduced with any of the polymerization reaction components, particularly with solvent, monomer and catalyst feed; and can adversely affect catalyst activity and stability. It can result in decreasing or even elimination of catalytic activity, particularly when an activator capable of ionizing the Group 8, 9 or 10 metal complex is also present.

The term "an inert functional group" means a functional group on a ligand or substituent which does not participate or react in the reaction. For example in the polymerization aspect of the present invention an inert functional group would not react with any of the monomers, the activator or the scavenger of the present invention. Similarly for the alkylation of the metal complex or the formation of the metal complex the inert functional group would not interfere with the alkylation reaction or the formation of the metal complex respectively.

As used in this specification an activatable ligand is a ligand removed or transformed by an activator. These include anionic substituents and/or bound ligands.

In the compounds of formula 11 above, preferably M is a Group 8, 9 or 10 metal. Preferably M is selected from the group of Group 8, 9 or 10 metals consisting of Fe, Co, Ni or Pd.

In the above compounds of formula I and II each R is independently selected from the group consisting of a hydrogen atom and hydrocarbyl radical. Preferably R is selected from the group consisting of $C_{1-10}$ alkyl or aryl radicals, most preferably $C_{1-4}$ radicals such as a bulky t-butyl radical and phenyl radicals. In the above formula I and II, $R^1$ and $R^2$ are independently selected from the group consisting of a hydrocarbyl radical preferably a phenyl radical which is unsubstituted or substituted by up to five hydrocarbyl radicals which may contain one or more inert functional groups, preferably $C_{1-4}$ alkyl radicals, or a $C_{1-10}$ alkyl radical, or two hydrocarbyl radicals taken together may form a ring, or tri alkyl silyl radical, preferably $C_{1-6}$, most preferably $C_{1-4}$ silyl radical. Preferably R may be a 2,6-diisopropyl phenyl radical or a trimethyl silyl radical. In the complex of formula II above, L is an activatable ligand preferably a halide atom or a $C_{1-6}$ alkyl or alkoxide radical, most preferably a halide atom (Cl or Br) and p is from 1 to 3, preferably 2 or 3.

In the compounds of formula I and II the unsaturated rings structure formed by Q taken together with W may form one or more a 5 to 10 membered ring(s) (i.e. Q contains from 4 to 9 atoms). As noted above not all of the atoms in the backbone of Q need to be carbon atoms. Q may contain one or more heteroatoms selected from the group consisting of an oxygen atom, a nitrogen atom, a sulfur atom and a boron atom. The resulting ring structure may be unsubstituted or up to fully substituted by one or more substituents selected from the group consisting of a halogen atom, preferably chlorine and a Ci alkyl radical.

In the above formulas I and II, R may be taken together with Q to form a cyclic hydrocarbyl structure, preferably an aromatic ring. If W is a sulfur atom then Q taken with the W may form rings such as thiophene, dithiole, thiazole and thiepin. If Q taken together with one R forms a cyclic hydrocarbyl then the structure may be benzothiophene. These unsaturated rings may be unsubstituted or up to fully substituted by one or more substituents selected from the group consisting of a halogen atom, preferably chlorine and a $C_{1-4}$ alkyl radical.

If W is an oxygen atom then Q taken with the W may form rings such as furan, oxazole, oxidiazole, pyran, dioxin, oxazine and oxepin. If Q taken together with one R forms a cyclic hydrocarbyl then the structure may be benzofuran, benzoxazole and benzoxazine. If both R's are taken together with Q and W the structure could be xanthene. These unsaturated rings may be unsubstituted or up to fully substituted by one or more substituents selected from the group consisting of a halogen atom, preferably chlorine and a $C_{1-4}$ alkyl radical.

If W is a phosphorus atom then the phosphorus homologues of the above oxygen and sulfur rings would be obtained.

In the above compounds, Z and Y may independently be selected from the group consisting of a carbon atom, an oxygen atom or a phosphorus atom. Preferably Z and Y are the same. Most preferably Z and Y are phosphorus atoms.

The metal complexes of the present invention may be prepared by reacting the ligand with a compound of MXn •A ($H_2O$), where X may be selected from the group consisting of halogen, $C_{1-6}$ alkoxide, nitrate or sulfate, preferably halide and most preferably chloride or bromide, and A is 0 or an integer from 1–6.

The reaction of the complex of formula I with the compound of the formula MXn •A ($H_2O$) may be conducted in a hydrocarbyl solvent or a polar solvent such as THF (tetrahydrofuran) or dichloromethane at temperature from 20° C. to 250° C., preferably from 20° C. to 120° C.

The resulting compound (i.e. formula II) may then be alkylated (either partially or fully). Some alkylating agents include alkyl aluminum reagents such as trialkyl aluminum, alkyl aluminum halides (i.e. $(R)_xAlX_{3-x}$ wherein R is a $C_1$ alkyl radical, X is a halogen, x is 1 or 2 and MAO as described below).

Solution polymerization processes are fairly well known in the art. These processes are conducted in the presence of an inert hydrocarbon solvent typically a $C_{5-12}$ hydrocarbon which may be unsubstituted or substituted by $C_{1-4}$ alkyl group such as pentane, hexane, heptane, octane, cyclohexane, methylcyclohexane or hydrogenated naphtha. An additional solvent is Isopar E ($C_{8-12}$ aliphatic solvent, Exxon Chemical Co.).

The polymerization may be conducted at temperatures from about 20° C. to about 250° C. Depending on the product being made, this temperature may be relatively low such as from 20° C. to about 180° C. The pressure of the reaction may be as high as about 15,000 psig for the older high pressure processes or may range from about 15 to 4,500 psig.

Suitable olefin monomers may be ethylene and $C_{3-20}$ mono- and di-olefins. Preferred monomers include ethylene and $C_{3-12}$ alpha olefins which are unsubstituted or substituted by up to two $C_{1-6}$ alkyl radicals, $C_{8-12}$. Illustrative non-limiting examples of such alpha olefins are one or more of propylene, 1-butene, 1-pentene, 1-hexene, 1-octene and 1-decene.

The reaction product of the present invention may be a co- or homopolymer of one or more alpha olefins. The polymers prepared in accordance with the present invention have a good molecular weight. That is, weight average molecular weight (Mw) will preferably be greater than about 50,000 ranging up to $10^6$, preferably $10^5$ to $10^6$.

The polyethylene polymers which may be prepared in accordance with the present invention typically comprise not less than 60, preferably not less than 70, most preferably not less than 80, weight % of ethylene and the balance of one or more $C_{4-10}$ alpha olefins, preferably selected from the group consisting of 1-butene, 1-hexene and 1-octene. The polyethylene prepared in accordance with the present invention may contain branching (e.g. one or more branches per 1000 carbon atoms, preferably 1–20 branches per 1000 carbon atoms, typically 1–10 branches per 1000 carbon atoms.

The activator may be selected from the group consisting of:

(i) an aluminoxane; and (ii) an activator capable of ionizing the Group 8, 9 or 10 metal complex (which may be used in combination with an alkylating activator). The aluminoxane activator may be of the formula $(R^{20})_2AlO(R^{20}AlO)_mAl(R^{20})_2$ wherein each $R^{20}$ is independently selected from the group consisting of $C_{1-20}$ hydrocarbyl radicals, m is from 0 to 50, and preferably $R^{20}$ is a $C_{1-4}$ alkyl radical and m is from 5 to 30. The aluminoxane activator may be used prior to the reaction but preferably in situ alkylation is typical (e.g. alkyl groups replacing leaving ligands, hydrogen or halide groups).

If the Group 8, 9 or 10 metal complex is activated only with aluminoxane, the amount of aluminoxane will depend on the reactivity of the alkylating agent. Activation with aluminoxane generally requires a molar ratio of aluminum in the activator to the Group 8, 9 or 10 metal in the complex from 50:1 to 1000:1. MAO may be at the lower end of the above noted range.

The activator of the present invention may be a combination of an alkylating activator which also serves as a scavenger other than aluminoxane in combination with an activator capable of ionizing the Group 8, 9 or 10 complex.

The alkylating activator (which may also serve as a scavenger) may be selected from the group consisting of: $(R)_pMgX_{2-p}$ wherein X is a halide, each R is independently selected from the group consisting of $C_{1-10}$ alkyl radicals, preferably $C_{1-8}$ alkyl radicals and p is 1 or 2; RLi wherein R is as defined above; $(R)_qZnX_{2-q}$ wherein R is as defined above, X is halogen and q is 1 or 2; $(R)_sAlX_{3-s}$ wherein R is as defined above, X is halogen and s is an integer from 1 to 3. Preferably in the above compounds, R is a $C_{1-4}$ alkyl radical and X is chlorine. Commercially available compounds include triethyl aluminum (TEAL), diethyl aluminum chloride (DEAC), dibutyl magnesium ($(Bu)_2Mg$) and butyl ethyl magnesium (BuEtMg or BuMgEt).

The activator capable of ionizing the Group 8, 9 or 10 metal complex may be selected from the group consisting of:

(i) compounds of the formula $[R^{15}]^+[B(R^{18})_4]^-$ wherein B is a boron atom, $R^{15}$ is a cyclic $C_{5-7}$ aromatic cation or a triphenyl methyl cation and each $R^{18}$ is independently selected from the group consisting of phenyl radicals which are unsubstituted or substituted with from 3 to 5 substituents selected from the group consisting of a fluorine atom, a $C_{1-4}$ alkyl or alkoxy radical which is unsubstituted or substituted by a fluorine atom; and a silyl radical of the formula —Si—$(R^{19})_3$ wherein each $R^{19}$ is independently selected from the group consisting of a hydrogen atom and a $C_{1-4}$ alkyl radical; and (ii) compounds of the formula $[(R^{16})_tZH]^+[B(R^{18})_4]^-$ wherein B is a boron atom, H is a hydrogen atom, Z is a nitrogen atom or phosphorus atom, t is 2 or 3 and $R^{16}$ is selected from the group consisting of $C_{1-8}$ alkyl radicals, a phenyl radical which is unsubstituted or substituted by up to three $C_{1-4}$ alkyl radicals, or one $R^{16}$ taken together with the nitrogen atom to form an anilinium radical and $R^8$ is as defined above; and (iii) compounds (activators) of the formula $B(R^{18})_3^{31}$ wherein $R^{18}$ is as defined above.

In the above compounds preferably $R^{18}$ is a pentafluorophenyl radical, $R^{15}$ is a triphenylmethyl cation, Z is a nitrogen atom and $R^{16}$ is a $C_{1-4}$ alkyl radical or $R^{16}$ taken together with the nitrogen atom forms an anilinium radical which is substituted by two $C_{1-4}$ alkyl radicals.

The activator capable of ionizing the Group 8, 9 or 10 metal complex abstracts one or more $L^1$ ligands so as to ionize the Group 8, 9 or 10 metal center into a cation, but not to covalently bond with the Group 8, 9 or 10 metal, and to provide sufficient distance between the ionized Group 8, 9 or 10 metal and the ionizing activator to permit a polymerizable olefin to enter the resulting active site.

Examples of compounds capable of ionizing the Group 8, 9 or 10 metal complex include the following compounds:

triethylammonium tetra(phenyl)boron,
tripropylammonium tetra(phenyl)boron,
tri(n-butyl)ammonium tetra(phenyl)boron,
trimethylammonium tetra(p-tolyl)boron,
trimethylammonium tetra(o-tolyl)boron,
tributylammonium tetra(pentafluorophenyl )boron,
tributylammonium tetra(pentafluorophenyl)boron,
tri(n-butyl)ammonium tetra (o-tolyl)boron
N,N-dimethylanilinium tetra(phenyl)boron,
N,N-diethylanilinium tetra(phenyl)boron,
N,N-diethylanilinium tetra(phenyl)n-butylboron,
N,N-2,4,6-pentamethylanilinium tetra(phenyl)boron
di-(isopropyl)ammonium tetra(pentafluorophenyl)boron,
dicyclohexylammonium tetra (phenyl)boron
triphenylphosphonium tetra)phenyl)boron,
tri(methylphenyl)phosphonium tetra(phenyl)boron,
tri(dimethylphenyl)phosphonium tetra(phenyl)boron,
tropillium tetrakispentafluorophenyl borate,
triphenylmethylium tetrakispentafluorophenyl borate,
benzene (diazonium) tetrakispentafluorophenyl borate,
tropillium phenyltris-pentafluorophenyl borate,
triphenylmethylium phenyl-trispentafluorophenyl borate,
benzene (diazonium) phenyltrispentafluorophenyl borate,
tropillium tetrakis (2,3,5,6-tetrafluorophenyl) borate,
triphenylmethylium tetrakis (2,3,5,6-tetrafluorophenyl) borate,
benzene (diazonium) tetrakis (3,4,5-trifluorophenyl) borate,
tropillium tetrakis (3,4,5-trifluorophenyl) borate,
benzene (diazonium) tetrakis (3,4,5-trifluorophenyl) borate,
tropillinum tetrakis (1,2,2-trifluoroethenyl) borate,
triphenylmethylium tetrakis (1,2,2-trifluoroethenyl) borate,
benzene (diazonium) tetrakis (1,2,2-trifluoroethenyl) borate,
tropillium tetrakis (2,3,4,5-tetrafluorophenyl) borate,
triphenylmethylium tetrakis (2,3,4,5-tetrafluorophenyl) borate, and
benzene (diazonium) tetrakis (2,3,4,5-tetrafluorophenyl) borate.

Readily commercially available activators which are capable of ionizing the Group 8, 9 or 10 metal complexes include:

N,N- dimethylaniliniumtetrakispentafluorophenyl borate;
triphenylmethylium tetrakispentafluorophenyl borate; and
trispentafluorophenyl boron.

If the Group 8, 9 or 10 metal complex is activated with a combination of an aluminum alkyl compound (generally other than aluminoxane), and a compound capable of ionizing the Group 8, 9 or 10 metal complex (e.g. activators (I) and (III) above) the molar ratios of Group 8, 9 or 10 metal:metal in the alkylating agent (e.g. Al); metalloid (e.g. boron or phosphorus) in the activator capable of ionizing the Group 8, 9 or 10 metal complex (e.g. boron) may range from 1:1:1 to 1:100:5. Preferably, the alkylating activator is premixed/reacted with the Group 8, 9 or 10 metal complex and the resulting alkylated species is then reacted with the activator capable of ionizing the Group 8, 9 or 10 metal complex.

In a solution polymerization the monomers are dissolved/dispersed in the solvent either prior to being fed to the reactor, or for gaseous monomers, the monomer may be fed to the reactor so that it will dissolve in the reaction mixture. Prior to mixing, the solvent and monomers are generally purified to remove polar moieties. The polar moieties or catalyst poisons include water, oxygen, metal impurities, etc. Preferably steps are taken before provision of such into the reaction vessel, for example by chemical treatment or careful separation techniques after or during the synthesis or preparation of the various components. The feedstock purification prior to introduction into the reaction solvent follows standard practices in the art (e.g. molecular sieves, alumina beds and oxygen removal catalysts) are used for the purification of ethylene, alpha olefin and optional diene. The solvent itself as well (e.g. cyclohexane and toluene) is similarly treated. In some instances, out of an abundance of caution, excess scavenging activators may be used in the polymerization process.

The feedstock may be heated prior to feeding into the reactor. However, in many instances it is desired to remove heat from the reactor so the feed stock may be at ambient temperature to help cool the reactor.

Generally, the catalyst components may be premixed in the solvent for the reaction or fed as separate streams to the reactor. In some instances premixing is desirable to provide a reaction time for the catalyst components prior to entering the reaction. Such an "in line mixing" technique is described in a number of patents in the name of Novacor Chemicals (International) S.A. (now known as NOVA Chemicals (International) S.A.) acquired from DuPont Canada Inc. For example it is described in U.S. Patent 5,589,555 issued Dec. 31, 1996.

The reactor may comprise a tube or serpentine reactor used in the "high pressure" polymerizations or it may comprise one or more reactors or autoclaves. It is well known that the use in series of two such reactors each of which may be operated so as to achieve different polymer molecular weight characteristics. The residence time in the reactor system will depend on the design and the capacity of the reactor. Generally the reactors should be operated under conditions to achieve a thorough mixing of the reactants. On leaving the reactor system the solvent is removed and the resulting polymer is finished in a conventional manner.

The present invention will now be illustrated by the following examples in which unless otherwise specified weight means weight % and parts means parts by weight (e.g. grams).

EXAMPLES

Materials: 2,6-dibromothiophene, diphenylphosphine ($Ph_2PH$), di-tert-butylphosphine chloride (t-$Bu_2PCl$), 2,5-Bis(5-tert-butyl-2-benzoxazolyl)thiophene (IIf), 2,6-di-isopropylaniline, 2,5-thiophenedicarboxaldehyde, iron (II) chloride (FeCl$_2$), iron (III) chloride (FeCl$_3$), cobalt chloride (CoCl$_2$), nickel (II) bromide (NiBr$_2$), n-Butyl lithium (n-BuLi, 1.6M in hexane), and trimethylsilyl azide (TMSN$_3$) were purchased from Aldrich Chemical Company Inc., Strem Chemical Inc. or Fisher Scientific. Solvents were prepared by passing through molecular sieves, de-oxo catalysts and alumina columns prior to use. Methylaluminoxane (PMAO-IP) (13.5 weight % of Al) was purchased from AKZO-NOBEL. Diimine-ferrous complex (VII) was synthesized as described in the literature (G. L. P. Britovsek, V. C. Gibson, B. S. Kimberley, P. J. Maddox, S. J. McTavish, G. A. Solan, A. J. P. White and D. J. Williams, J. Chem. Soc. Chem. Commun., 1998, 849 and B. L. Small, M. Brookhart and A. M. A. Bennett, J. Am. Chem. Soc., 120, 4049, 1998). The anhydrous toluene was purchased from Aldrich and purified over molecular sieves prior to use. B(C$_6$F$_5$)$_3$ was purchased from Boulder Scientific Inc. and used without further purification. Trityl borate was purchased from Asahi Glass Inc., lot #980224.

Measurements: NMR spectra were recorded using a Bruker 200 MHz spectrometer. $^1$H NMR chemical shifts were reported with reference to tetramethylsilane. Polymer molecular weights and molecular weight distributions were measured by GPC (Waters 150- C) at 140° C. in 1,2,4-trichlorobenzene calibrated using polyethylene standards. DSC was conducted on a DSC 220 C from Seiko Instruments. The heating rate is 10° C./minute from 0 to 200° C. FT-IR was conducted on a Nicolet Model 750 Magna IR spectrometer. Operation: All synthesis and catalyst preparations were performed under nitrogen or argon atmospheres using standard Schlenk techniques or in a dry-box.

Example 1

Synthesis of Bis(2,5-di-tert-butylphosphino) thiophene (Ia)

To a THF (50 mL) solution of 2,5-dibromothiophene (5.00 g, 20.7 mmol) at −78° C. was added slowly a THF (30 mL) solution of n-BuLi (26.9 mL, 1.6 M in hexane, 41.3 mmol). The color of the solution changed from clear colorless to pale blue, then to pink, then to green. After 95% BuLi addition, the greenish solution gelated. The reaction mixture was then allowed to warm to −50° C. over 1 hour and a THF (25 mL) solution of t-Bu$_2$PCl (7.47 g, 41.3 mmol) was added. The color of the reaction solution changed to pale yellow. The reaction mixture was warmed to room temperature and stirred for 12 hours. All volatiles were then removed under vacuum. The resulting residue was dissolved in heptane (50 mL) and LiBr was removed by filtration. When the heptane and some volatile impurities were removed at 50° C. in vacuo, a brown solid was obtained. The pure product, a pale pink solid, was obtained from a crystallization process in a hexane/toluene (3:1) solution at −35° C. Yield is 36%. $^1$H NMR (toluene-d$_8$, δ): 1.20 (d, J=11.8 Hz, 36H), 7.34–7.38 (m, 2H). The purity and molecular weight (M$^+$= 372) were confirmed by GC-MS.

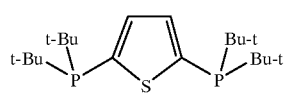

(Ia)

Example 2

Synthesis of 2,5-bis (diphenylshosphino)thiophene (Ib)

A THF (50 mL) solution of diphenylphosphine (2.53 g, 13.6 mmol) was treated with n-BuLi (8.5 mL, 1.6 M, 13.6 mmol) using a drop-wise addition. The reaction mixture was allowed to stir 20 minutes and was then added to a solution of 2,5-dibromothiophene (1.63 g, 6.79 mmol) at room temperature resulting in a yellow solution. The reaction was allowed to warm up to room temperature for 2 hours. The product (2.92 g, 95% yield) was purified by a crystallization process in toluene. $^1$H NMR (toluene-d$_8$, δ): 7.02–6.97 (m, 12H), 7.12–7.09 (m, 2H), 7.30–7.39 (m, 8H). The purity and molecular weight (M$^+$=452) were confirmed by GC-MS.

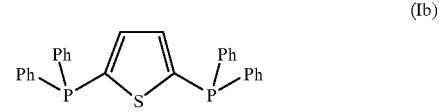

(Ib)

Example 3

Synthesis of 2,5-(t-Bu$_2$P=NTMS)$_2$thiophene (IIa)

A 200 mL Schlenk flask was fitted with a condenser, a nitrogen inlet, a gas outlet bubbler and a TMSN$_3$ addition line. The flask was charged with 2,5-(t-Bu$_2$P)$_2$thiophene (Ia) (1.29 g, 3.47 mmol). The TMSN$_3$ line was charged with TMSN$_3$ (7.0 mL, 52.7 mmol) through a syringe. At room temperature, 3 mL of TMSN$_3$ was injected into the flask and the mixture was heated to 95° C. The remaining TMSN$_3$ was added to the reaction at 95° C. As the addition occurred, nitrogen was evolved. After the addition was completed, the reaction mixture was kept for an additional 2 hours at 110° C. When the excess of TMSN$_3$ was removed under vacuum, a white solid (1.87 g, 98% yield) was obtained. $^1$H NMR (toluene-d$_8$, δ): 0.43 (s, 18H), 1.12 (d, J=14.7Hz, 36H), 7.34–7.38 (m,2H).

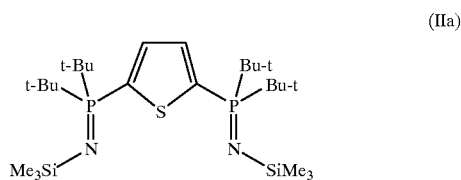

(IIa)

Example 4

Synthesis of 2,5-(Ph$_2$P=NTMS)$_2$thiophene (IIb)

A 200 mL Schlenk flask was fitted with a condenser, a nitrogen inlet, a gas outlet bubbler and a TMSN$_3$ addition line. The flask was charged with 2,5-(Ph$_2$P)$_2$thiophene (Ib) (2.92 g, 6.45 mmol). The TMSN$_3$ line was charged with TMSN$_3$ (6.0 mL, 45.2 mmol) through a syringe. At room temperature, 3 mL of TMSN$_3$ was injected into the flask and the mixture was heated to 95° C. The remaining TMSN$_3$ was added to the reaction at 95° C. As the addition occurred, nitrogen was evolved. After the addition was completed, the reaction mixture was kept for an additional 2 hours at 115° C. When the excess of TMSN$_3$ was removed under vacuum, a white solid (4.0 g, 98% yield) was obtained. $^1$H NMR (toluene-d$_8$, δ): 0.31 (s, 18H), 6.99–7.04 (m, 12H), 7.11–7.23 (m, 2H), 7.64–7.74 (m, 8H).

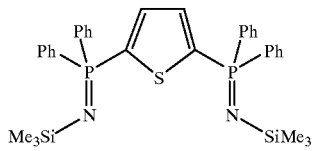

(IIb)

Example 5

Synthesis of 2,5-(Ph$_2$P=N-PBu$^t_2$)thiophene (IIc)

The toluene solution of IIb (200 mg, 0.37 mmol) and chlorodiphenylphosphine (169 mg, 0.76 mmol) was refluxed for 25 hours. When the toluene was removed in vacuo, a pale yellow solid (280 mg, 99% yield) was obtained. $^1$H NMR (toluene-d$_8$, δ): 1.25 (d, J =10.6, 36H), 6.92–7.04 (m, 12H), 7.54–7.65 (m, 8H), 8.50 -8.60 (m, 2H).

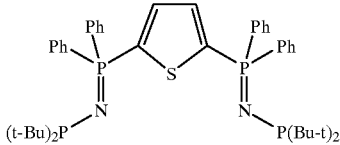

(IIc)

Example 6

Synthesis of 2,5-(Ph$_2$P=N-P(Bu$^t_2$)=NTMS)$_2$thiophene (IId)

A 200 mL Schlenk flask was fitted with a condenser, a nitrogen inlet, a gas outlet bubbler and a TMSN$_3$ addition line. The flask was charged with 2,5-(Ph$_2$P=N-P(Bu$^t_2$))$_2$thiophene (IIc) (0.28 g, 0.37 mmol). The TMSN$_3$ line was charged with TMSN$_3$ (2.5 mL, 18.8 mmol) through a syringe. At room temperature, 1 mL of TMSN$_3$ was injected into the flask and the mixture was heated to 95° C. The remaining TMSN$_3$ was added to the reaction at 95° C. As the addition occurred, nitrogen was evolved. After the addition was completed, the reaction mixture was kept for an additional 2 hours at 115° C. When the excess of TMSN$_3$ was removed under vacuum, a pale yellow solid (0.33 g, 95% yield) was obtained. $^1$H NMR (toluene-d$_8$, δ): 0.33 (s, 18H), 1.15 (d, J=10.3 Hz, 36H), 6.97–7.10 (m, 12H), 7.11–7.23 (m, 8H), 8.07–8.25 (m, 2H).

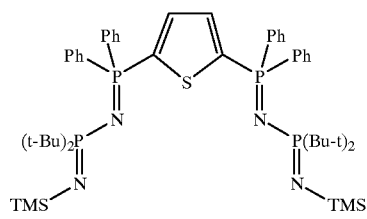

(IId)

Example 7

Synthesis of 2,5-thiophenedicarboxaldehydebis(2,6-diisopropyl)phenyl) (IIe)

In a 500 mL Schlenk flask, 2,5-thiophenedicarboxaldehyde (2 g, 14.3 mmol), 2,6-diisopropylaniline (5.13 g, 29 mmol) and formic acid (1 mL) were placed in methanol (100 mL). The mixture was stirred at room temperature overnight. A yellow solid (4.5 g, yield 91 %) was obtained when the reaction mixture was filtered off, washed with MeOH and dried. $^1$H NMR (toluene-d$_8$, δ): 1.21 (d, J =6.9 Hz, 24H), 3.02 (m, 4H), 7.1–7.2 (m, 6H), 7.49 (s, 2H), 8.30 (s, 2H).

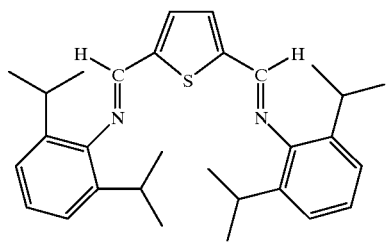

(IIe)

Examples 8–13

Synthesis of Catalyst Precursors

General Procedure: The ligand (2,5-(t-Bu$_2$P=NTMS)$_2$thiophene (IIa), 1 eq.) and a metal salt (FeCl$_2$, CoCl$_2$, FeBr$_3$, FeCl$_3$ or NiBr$_2$) were added together in a Schlenk flask in a dry-box. Then the flask was charged with THF (30 mL) or dichloromethane (CH$_2$Cl$_2$, 30 mL). The mixture was stirred for several hours until no metal salts were observed in the flask. The reaction solution was filtered to remove some insoluble polymeric materials and was concentrated. Heptane (5 mL) was added to precipitate the complex. The resultant solid was filtered and washed with heptane and dried in vacuo.

Example 8

Fe(III) Complex (IIIa) from IIa and FeCl$_3$

Isolated as a beige solid (Yield: 98%). $^1$H NMR (toluene-d8, δ): 0.42 (s, br, 18H), 1.12 (d, br, J=14.7 Hz, 36H), 7.37 (s, br, 2H).

Example 9

Fe(II) Complex (IIIb) from IIa and FeCl$_2$

Isolated as a white solid (Yield: 85%). $^1$H NMR (THF-d8, all peaks appear as singlets due to their broadness, δ): 0.09 (s, br, 18H), 1.25 (d, J=14.6 Hz, 36H ), 7.65 (s, br, 2H).

Example 10

Co(II) Complex (IIIc) from IIa and CoCl$_2$

Isolated as a blue solid (Yield: 100%). $^1$H NMR (THF-d8, all peaks appear as singlets due to their broadness, δ): 0.09 (s, br, 18H), 1.25 (d, br, J=14.8 Hz, 36H), 7.65 (s, br, 2H).

Example 11

Fe(III) Complex (IV) from IId and FeCl$_3$

Isolated as a pale amber solid (Yield: 84%). $^1$H NMR (THF-d8, δ): -0.10 (s, 18H), 1.29 (br, 36H), 7.20 (s, br, 12H), 7.77 (s, br, 8H).

Example 12

Fe(III) Complex (V) from IIe and FeCl$_2$

Isolated as an yellow solid (Yield: 98%). $^1$H NMR (THF-d8, all peaks appear as singlets due to their broadness, δ): 1.13 (br, 24H), 3.1 (br, 4H), 7.08 (br, 8H), 7.9 (s, br, 2H).

Example 13

Fe(III)) Complex (VI) from IIf and FeBr$_3$

Isolated as an yellow solid (Yield: 98%). $^1$H NMR (THF-d8, all peaks appear as singlets due to their broadness, δ): 0.62 (s, br), 6.15 (s, br).

Polymerization Results

In the examples, the pressures given are gauge pressures. The following abbreviations and terms are used:

Branching: reported as the number of methyl groups per 1000 methylene groups in the polymer. It is determined by FT-IR.

Polydispersity: weight average molecular weight (Mw) divided by number average molecular weight (Mn).

DSC: differential scanning calorimetry.

GPC: gel permeation chromatography.

MeOH: methanol.

PMAO-IP: a type of polymethylaluminoxane.

All the polymerization experiments described below were conducted using a 500 mL Autoclave Engineers Zipperclave reactor. All the chemicals (solvent, catalyst and cocatalyst) were fed into the reactor batchwise except ethylene which was fed on demand. No product was removed during the polymerization reaction. As are known to those skilled in the art, all the feed streams were purified prior to feeding into the reactor by contact with various absorption media to remove catalysts killing impurities such as water, oxygen, sulfur and polar materials. All components were stored and manipulated under an atmosphere of purified argon or nitrogen. The reactor uses a programmable logic control (PLC) system with Wonderware 5.1 software for the process control. Ethylene polymerizations were performed in the reactor equipped with an air driven stirrer and an automatic temperature control system.

Polymerization temperature was 50° C. for slurry polymerizations and 140 and 160° C. for solution polymerizations. The polymerization reaction time varied from 10 to 30 minutes for each experiment. The reaction was terminated by adding 5 mL of methanol to the reactor and the polymer was recovered by evaporation of the toluene. The polymerization activities were calculated based on weight of the polymer produced.

Slurry Polymerization

Example 14

The Iron Complex (IIIa) With MAO Activation

Toluene (216 mL) was transferred into the reactor. The solvent was heated to 50° C. and saturated with 300 psig of ethylene. PMAO-IP (3.83 mmol, 0.85 mL) was first injected into the reactor. After one minute, the catalyst (IIa) (64.8 umol, 46.1 mg) dissolved in toluene (12.2 mL) was injected into the reactor. The polymerization happened slowly with no temperature increase. The reaction was terminated by adding 5 mL of MeOH after 30 minutes. The polymer was dried. Yield=2.6 g. Activity=80.0 gPE/mmolcat*hr. Mw=353.7*10$^3$. PD=3.5. Tm=133.0° C.

Solution Polymerization

Example 15

The Iron Complex (IIIa) with MAO Activation

Toluene (216 mL) was transferred into the reactor. The solvent was heated to 140° C. and saturated with 286 psig of ethylene. PMAO-IP (3.83 mmol, 0.85 mL) was first injected into the reactor. After one minute, the catalyst (IIa) (64.8 umol, 45.9 mg) dissolved in toluene (12.2 mL) was injected into the reactor. The polymerization happened immediately and reaction temperature increased to 147° C. within 30 seconds. The polymerization activity decreased dramatically after 1.5 minutes. The reaction was terminated by adding 5 mL of MeOH after 10 minutes. The polymer was dried.

Yield=5.1 g. Activity=473.0 g PE/mmolcat*hr. Mw=470.3*10$^3$. PD=1.9. Tm=135.8° C.

Example 16

The Iron Complex (IIIa) With MAO Activation

Toluene (216 mL) was transferred into the reactor. The solvent was heated to 160° C. and saturated with 200 psig of ethylene. PMAO-IP (2,6 mmol, 0.60 mL) was first injected into the reactor. After one minute, the catalyst (IIa) (43.2 umol, 30.6 mg) dissolved in toluene (12.2 mL) was injected into the reactor. The polymerization happened immediately and with no temperature increase. The polymerization activity decreased dramatically after 30 seconds. The reaction was terminated by adding 5 mL of MeOH after 10 minutes. The polymer was dried.

Yield=3.3 g. Activity=458.5 g PE/mmolcat*hr. Mw=560.8*103. PD=2.6. Tm=132.9° C.

Example 17

The Iron Complex (IIIa) with MAO In-Situ Alkylation And B(C$_6$F$_5$)$_3$ Activation Toluene (216 mL) was transferred into the reactor with 0.05 mL of PMAO-IP (216.0 umol) in 10 mL of toluene. The solution was heated to 140° C. and saturated with 286 psig of ethylene. The catalyst (IIIa) (64.8 umol, 45.8 mg) was dissolved in toluene (11.8 mL) and transferred into a catalyst injection bomb and then mixed with PMAO-IP (1.35 mmol, 0.3 ML). B(C$_6$F$_5$)$_3$ (67.9 umol, 34.8 mg) was dissolved in toluene (12.4 mL) and loaded into a cocatalyst injection bomb. The catalyst and cocatalyst were injected into reactor simultaneously. The polymerization happened immediately with no temperature increase. The ethylene consumption was decreased after 30 seconds and dropped to zero after 2 minutes. The reaction was terminated by adding 5 mL of MeOH after 10 minutes. The polymer was dried.

Yield=9.7 g. Activity=900.3 g PE/mmolcat*hr. Mw=495.9*10$^{3\cdot}$ PD=2.1. Tm=134.7° C.

Example 18

The Iron Complex (IIIa) with MAO In-Situ Alkylation And [CPh$_3$][B(C$_6$F$_5$)$_4$] Activation Toluene (216 mL) was transferred into the reactor with 0.05 mL of PMAO-IP (216.0 umol) in 10 mL of toluene. The solution was heated to 140° C. and saturated with 286 psig of ethylene. The catalyst (IIIa) (64.8 umol, 45.5 mg) was dissolved in toluene (11.8 mL) and transferred into a catalyst injection bomb and then mixed with PMAO-IP (1.35 mmol, 0.3 mL). [CPh$_3$][B(C$_6$F$_5$)$_4$] (68.0 umol, 62.3 mg) was dissolved in toluene (12.4 mL) and loaded into a cocatalyst injection bomb. The catalyst and cocatalyst were injected into reactor simultaneously. The polymerization happened immediately and polymerization temperature increased to 170° C. within 30 seconds. The polymerization activity decreased after 3 minutes. The reaction was terminated by adding 5 mL of MeOH after 10 minutes. The polymer was dried.

Yield=10.0 g. Activity=934.9 g PE/mmolcat*hr. Mw=749.3*10$^3$. PD=2.0. Tm=134.3° C.

Example 19

The Iron Complex (IIIa) with MAO Activation for Ethylene and 1-Octene Copolymerization

Toluene (216 mL) and 40 mL of 1-octene were transferred into the reactor with 0.05 mL of PMAO-IP (216.0 umol) in 10 mL of toluene. The solution was heated to 140° C. and saturated with 286 psig of ethylene. PMAO-IP (3.83 mmol, 0.85 mL) was injected into the reactor. After one minute, the catalyst (IIIa) (64.8 umol, 45.6 mg) was dissolved in toluene and injected to the reactor. The polymerization happened immediately and polymerization temperature increased to 150° C. within 30 seconds. The reaction was terminated by adding 5 mL of MeOH after 10 minutes. The polymer was dried.

Yield=6.0 g. Activity=555.0 gPE/mmolcat*hr. Mw=790.7*10$^3$. PD=2.0. Tm=115° C. 6.8 Br/1000C detected by FT-IR.

Example 20

The Iron Complex (IIIb) with MAO Activation

Toluene (216 mL) was transferred into the reactor. The solvent was heated to 140° C. and saturated with 286 psig of ethylene. PMAO-IP (3.83 mmol, 0.85 mL) was first injected into the reactor. After one minute, the catalyst (IIIb) (64.8 umol, 43.7 mg) dissolved in toluene (12.2 mL) was injected into the reactor. The polymerization happened immediately and reaction temperature increased to 145° C. within 30 seconds. The polymerization activity decreased dramatically after 1 minutes. The reaction was terminated by adding 5 mL of MeOH after 10 minutes. The polymer was dried.

Yield=3.7 g. Activity=342.4 g PE/mmolcat*hr. Mw=975.6*10$^3$. PD=1.7. Tm=135.1° C.

Example 21

The Cobalt Complex (IIIc) with MAO Activation

Toluene (216 mL) was transferred into the reactor. The solvent was heated to 140° C. and saturated with 286 psig of ethylene. PMAO-IP (3.83 mmol, 0.85 mL) was first injected into the reactor. After one minute, the catalyst (IIIc) (64.8 umol, 43.7 mg) dissolved in toluene (12.2 mL) was injected into the reactor. The polymerization happened slowly with no temperature increase. The polymerization activity decreased dramatically after 2 minutes. The reaction was terminated by adding 5 mL of MeOH after 10 minutes. The polymer was dried.

Yield=3.8 g. Activity=351.4 g PE/mmolcat*hr. Mw=605.7*10$^3$. PD=1.85. Tm=134.3° C.

Example 22

The Iron Complex (V) with MAO Activation

Toluene (216 mL) was transferred into the reactor. The solvent was heated to 140° C. and saturated with 286 psig of ethylene. PMAO-IP (3.83 mmol, 0.85 mL) was first injected into the reactor. After one minute, the catalyst (V) (64.8 umol, 38.0 mg) dissolved in toluene (12.2 mL) was injected into the reactor. The polymerization happened immediately and reaction temperature increased to 145° C. within 30 seconds. The polymerization activity decreased dramatically after 1 minute. The reaction was terminated by adding 5 mL of MeOH after 10 minutes. The polymer was dried.

Yield=3.5 g. Activity=322.9 g PE/mmolcat*hr. Mw=617.3*10$^3$. PD=2.46. Tm=134.8° C.

Example 23

The Iron Complex (VI) with MAO Activation

Toluene (216 mL) was transferred into the reactor. The solvent was heated to 140° C. and saturated with 286 psig of ethylene. PMAO-IP (3.83 mmol, 0.85 mL) was first injected into the reactor. After one minute, the catalyst (VI) (64.8 umol, 46.9 mg) dissolved in toluene (12.2 mL) was injected into the reactor. The polymerization happened immediately and reaction temperature increased to 150° C. within 30 seconds. The polymerization activity decreased dramatically after 1.5 minutes. The reaction was terminated by adding 5 mL of MeOH after 10 minutes. The polymer was dried.

Yield=4.1 g. Activity=381.2 g PE/mmolcat*hr. Mw=600.1*10$^3$. PD=1.86. Tm=134.3° C.

Comparative Example

The Iron Complex (Vl) with MAO Activation

Toluene (216 mL) was transferred into the reactor. The solvent was heated to 140° C. and saturated with 286 psig of ethylene. PMAO-IP (3.83 mmol, 0.85 mL) was first injected into the reactor. After one minute, the catalyst (VII) (64.8 umol, 39.2 mg) dissolved in toluene (12.2 mL) was injected into the reactor. The polymerization happened immediately and reaction temperature increased to 162° C. within 30 seconds. The polymerization activity decreased dramatically after 3 minutes. The reaction was terminated by adding 5 mL of MeOH after 10 minutes. The polymer was dried.

Yield=10.3 g. Activity=960.0 g PE/mmolcat*hr. Mw=457.5*10$^3$. PD=45.62. Tm=99–123° C. multi-peaks.

What is claimed is:

1. A ligand of formula I:

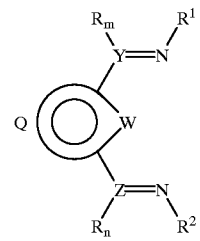

wherein W is selected from the group consisting of a sulfur atom, an oxygen atom and a phosphorus atom; Y and Z are independently selected from the group consisting of a carbon atom, a phosphorus atom and a sulfur atom; when Y is phosphorus m is 2, when Y is carbon or sulfur m is 1; when Z is phosphorus n is 2, when Z is carbon or sulfur n is 1; each R is independently selected from the group consisting of a hydrogen atom, and a hydrocarbyl radical or R taken together with Q may form a cyclic hydrocarbyl; $R^1$ and $R^2$ are independently selected from the group consisting of a hydrogen atom, a substituted or unsubstituted hydrocarbyl radical which may contain one or more heteroatoms which may be bonded directly or indirectly to the nitrogen atoms and a tri-$C_{1-4}$ alkyl silyl radical; Q is a divalent unsaturated hydrocarbyl radical or a divalent radical comprising hydrogen, carbon and one or more heteroatoms selected from the group consisting of an oxygen atom, a nitrogen atom, a sulfur atom and a boron atom, and Q when taken together with W forms one or more unsaturated rings, which unsaturated cyclic rings may be unsubstituted or may be fully substituted by one or more substituents independently selected from the group consisting of a halogen atom and an alkyl radical.

2. The ligand according to claim 1, wherein each R is independently selected from the group consisting of a hydrogen atom and a $C_{1-10}$ alkyl or aryl radical.

3. The ligand according to claim 2, wherein $R^1$ and $R^2$ are independently selected from the group consisting of $C_{1-10}$ alkyl radicals, tri $C_{1-6}$ alkyl silyl radicals and phenyl radicals which are unsubstituted or substituted by up to five substituents independently selected from the group consisting of a Coo alkyl radicals, halides and inert functional groups.

4. The ligand according to claim 3, wherein Y and Z are the same.

5. The ligand according to claim 4, wherein $R^1$ and $R^2$ are independently selected from the group consisting of a trimethyl silyl radical and a 2,6-di-isopropyl phenyl radical.

6. The ligand according to claim 5, wherein Y and Z are both a phosphorus atom.

* * * * *